US00PP28047P3

(12) United States Plant Patent
Castellarin et al.

(10) Patent No.: US PP28,047 P3
(45) Date of Patent: May 23, 2017

(54) GRAPEVINE NAMED 'CABERNET VOLOS'

(50) Latin Name: ***Vitis×vinifera* (hybrid)**
Varietal Denomination: CABERNET VOLOS

(71) Applicants: Università degli Studi di Udine, Udine UD (IT); Istituto di Genomica Applicata, Udine UD (IT)

(72) Inventors: Simone Diego Castellarin, Vancouver (CA); Guido Cipriani, Faedis (IT); Gabriele Di Gaspero, Cividale del Friuli UD (IT); Michele Morgante, Tricesimo UD (IT); Enrico Peterlunger, Codroipo UD (IT); Raffaele Testolin, Udine (IT)

(73) Assignees: Università degli Studi di Udine, Udine (IT); Istituto di Genomica Applicata, Udine (IT)

( * ) Notice: Subject to any disclaimer, the term of this patent is extended or adjusted under 35 U.S.C. 154(b) by 0 days.

(21) Appl. No.: 14/545,113

(22) Filed: Mar. 27, 2015

(65) Prior Publication Data

US 2016/0242336 P1 Aug. 18, 2016

(30) Foreign Application Priority Data

Feb. 13, 2015 (QZ) ..... PBR 2015/0362

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Foley & Lardner LLP

(57) ABSTRACT

A new and distinct variety of grapevine named 'CABERNET VOLOS', primarily suited to the growing conditions of the temperate regions, and characterized by its medium vigor; semi-erect growth habit; medium, pentagonal to circular shaped leaves; short-medium, dense, cylindrical berry clusters; dark blue berries with soft to slightly firm berry flesh, herbaceous taste, and no flesh coloration; and resistance to winter temperatures (to −24° C.), resistance to downy mildew, and tolerance to powdery mildew.

4 Drawing Sheets

Latin name of the genus and species of the plant claimed: *Vitis×vinifera* (hybrid).

Variety name: 'CABERNET VOLOS'.

BACKGROUND OF THE INVENTION

The present invention relates to a new and distinct summer/fall bearing grapevine variety, botanically known as *Vitis×vinifera*, and hereinafter referred to by the name 'CABERNET VOLOS'.

The new grapevine 'CABERNET VOLOS' is a product of a controlled breeding program conducted by the inventors in Udine, Italy. The objective of the breeding program was to develop a new grapevine variety particularly characterized by resistance to cold (<−20° C.), resistance to downy mildew (*Plasmopara viticola*), and tolerance to powdery mildew (*Uncinula necator*).

The new grapevine 'CABERNET VOLOS' originated from a cross made by the inventors in 2002 in Udine, Italy. The female or seed parent is the grapevine variety, *Vitis vinifera* cv. 'Cabernet Sauvignon' (unpatented), and the male or pollen parent is the grapevine variety, *Vitis* cv. '20/3' (Bianca×SK77-4/5) (unpatented).

The new grapevine 'CABERNET VOLOS' was discovered and selected by the inventor as a single flowering plant within the progeny of the stated cross in a controlled environment in 2002 in Udine, Italy. Asexual reproduction of the new grapevine variety by grafting was first performed in February 2004 in Rauscedo, Friuli Venezia Giulia region, Italy, and has demonstrated that the combination of characteristics as herein disclosed for the new cultivar are firmly fixed and retained through successive generations of asexual reproduction. The new cultivar reproduces true to type.

SUMMARY OF THE INVENTION

'CABERNET VOLOS' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required for it to produce and maintain a strong vigorous plant with consistent fruit production from April through November on primocanes and in the ensuing year from April through November on the floricanes.

The following traits have been repeatedly observed and are determined to be unique characteristics of 'CABERNET VOLOS', which in combination distinguish this grapevine plant as a new and distinct variety.

1. Medium vigor;
2. Semi-erect growth habit;
3. Medium size, pentagonal to circular shaped leaves with medium green upper surfaces and pale green lower surfaces and medium texture;
4. Short-medium size, dense, cylindrical shaped berry clusters with one middle-size wing; dark blue berries with soft to slightly firm flesh, herbaceous taste, and no flesh coloration; primarily used for wine; maturing in Mid-late September (Middle Friuli, North-Eastern Italy);

5. Primocanes and floricanes with elliptic cross section, brownish color, no lenticels, and short-middle internodes (13-14 cm with diameter: 9-10 mm);
6. Harvesting time of Mid-late September (Middle Friuli, North-Eastern Italy); and
7. Resistance to winter temperature (−24° C.), resistance to downy mildew, and tolerance to powdery mildew.

Plants of the new grapevine 'CABERNET VOLOS' differ from plants of the parents, *Vitis vinifera* 'Cabernet Sauvignon' (unpatented) and *Vitis* cross '20/3' (unpatented), in the following characteristics described in Table 1.

TABLE 1

Comparison with parent varities

| Characteristic | New Cultivar 'CABERNET VOLOS' | Female Parent 'Cabernet Sauvignon' (unpatented) | Male Parent '20/3' (unpatented) |
|---|---|---|---|
| vigour: growth habit | medium semi-erect | strong horizontal | medium semi-erect |
| leaf | medium size, medium green color (upper surface), pale green color (lower surface), pentagonal and circular shape, medium texture, no hairs in both surfaces. | medium size, medium green color (both upper and lower surface), low hair density in both surfaces, circular shape, medium texture | Medium size, light green color (upper surface), green color (lower surface), no hairs in both surfaces, wedge-shaped-kidney-shaped, medium texture |
| cluster | short-medium size cluster, cylindrical with one middle-size wing, dense, berry skin with dark-blu color, soft to slightly firm flesh, herbaceous taste, no flesh coloration | Very low weight, cylindrical shape with 1-2 wings, medium bunch density, berry skin with blue black color, soft flesh, neutral taste, no to very weak flesh coloration | low weight, conical, with 1-2 wings, medium dense, berry skin with green-yellow color, slightly firm flesh, neutral taste, no flesh coloration |
| primocane and floricane | ellictic cross section, brownish colour, lenticels: absent, short-middle internodes (13-14 cm), diameter: 8 9-10 mm | circular cross section, brownish color, lenticels: absent, medium internodes, diameter small (about 8 mm) | oblate cross section, brownish color, lenticels: absent, medium internodes, diameter small (about 8 mm) |
| harvesting time | Mid-late September (Middle Friuli, North-Eastern Italy) | late (1st week of October in Middle Friuli, North-Eastern Italy) | Early (last decade August, Middle Friuli, North-Eastern Italy) |
| resistances | resistant to winter temperature (−24° C.), resistant to downy mildew, tolerant to powdery mildew. | Resistance to winter temperature not checked, susceptible to downy mildew, susceptible to powdery mildew | resistant to winter temperature not checked, resistant to downy mildew, resistant to powdery mildew |

Of the many commercial cultivars known to the present inventor, the most similar to the new grapevine 'CABERNET VOLOS' is the female parent 'Cabernet Sauvignon', to which a comparison has been provided above.

BRIEF DESCRIPTION OF THE PHOTOGRAPHS

The accompanying photographs illustrate the overall appearance of the new grapevine 'CABERNET VOLOS' showing the colors as true as is reasonably possible with colored reproductions of this type. Colors in the photographs may differ slightly from the color values cited in the detailed botanical description, which accurately describe the color of 'CABERNET VOLOS'.

DETAILED BOTANICAL DESCRIPTION

Figure 1A:
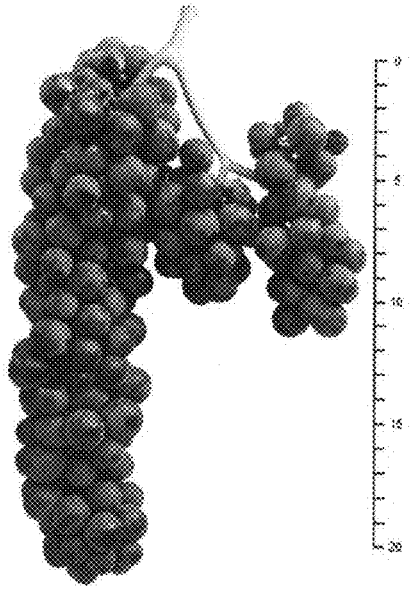
FIG. 1A and FIG. 1B show a typical fruit cluster of 'CABERNET VOLOS' taken on Sep. 10, 2012, in Udine, Italy
Figure 1B:
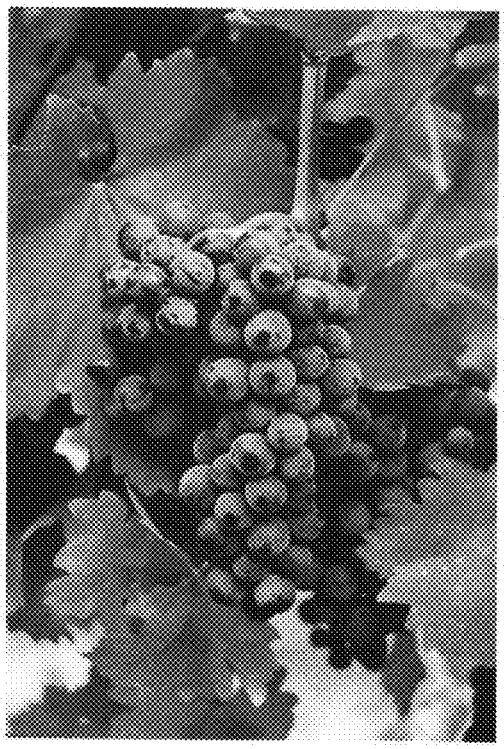
Figure 2:
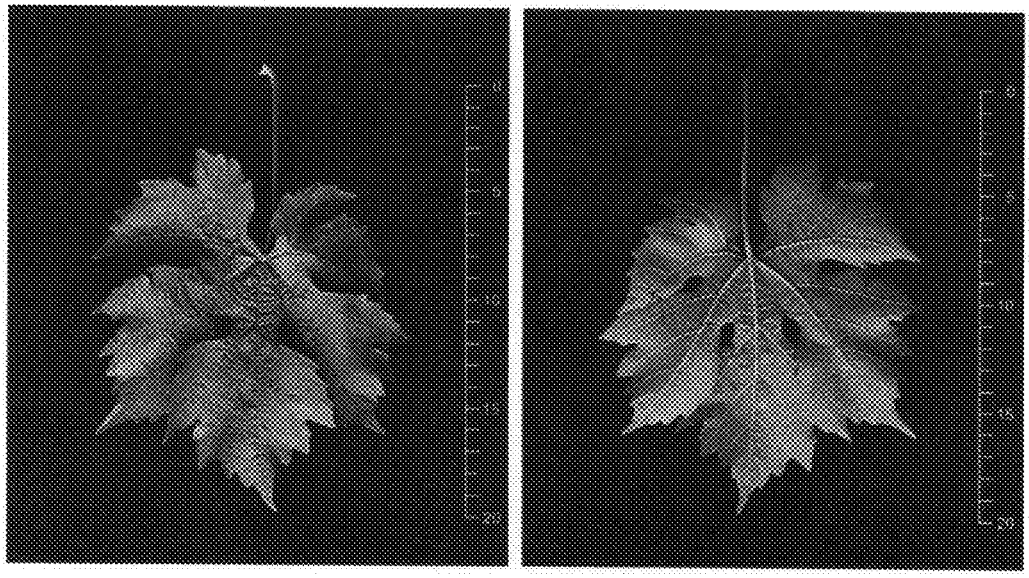
FIG. 2 shows a typical mature leaf (upper surface, left and lower surface, right) of 'CABERNET VOLOS' taken on Jun. 15, 2012, in Udine, Italy.
Figure 3:
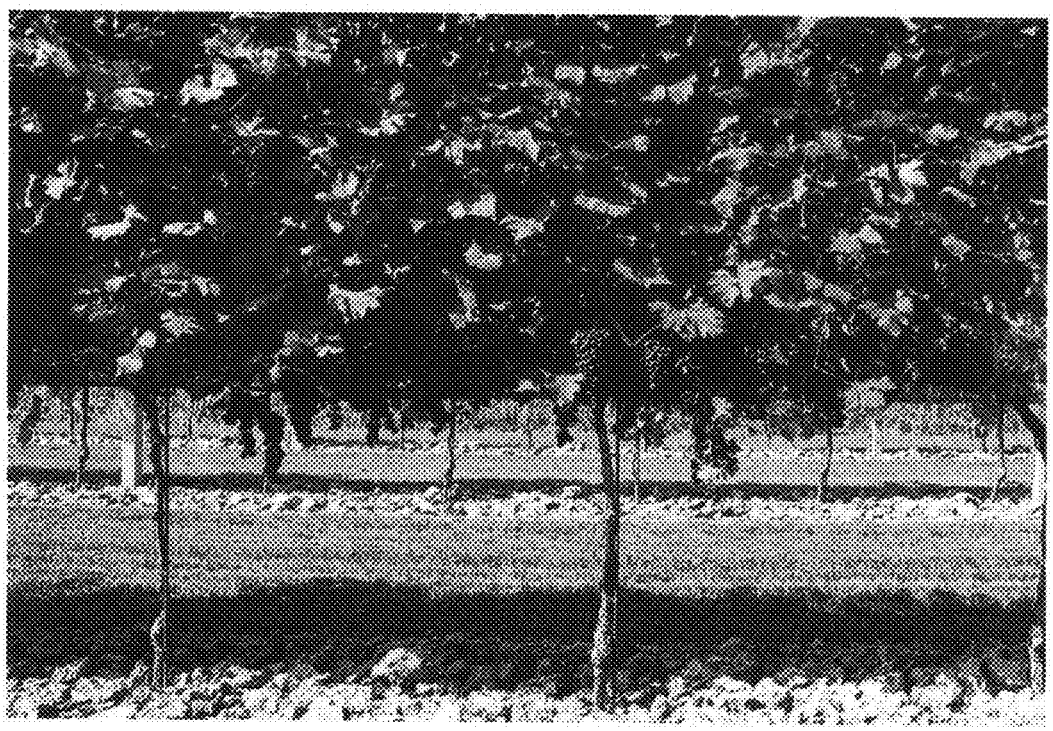
FIG. 3 shows a typical mature vine of 'CABERNET VOLOS' taken on Aug. 3, 2012.
Figure 4:
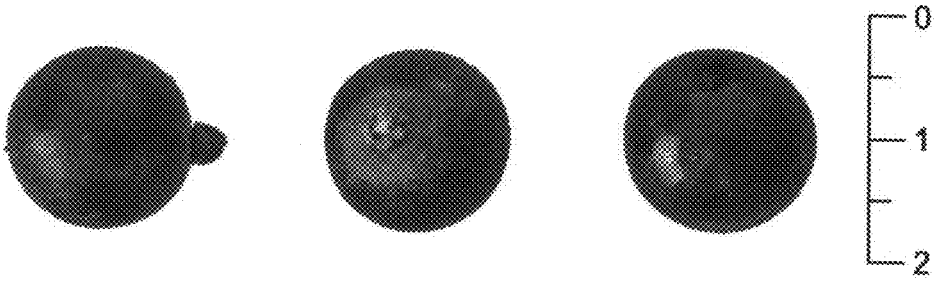
FIG. 4 shows a close-up view of mature fruit of 'CABERNET VOLOS' taken on Sep. 10, 2012, in Udine, Italy.

The following description of 'CABERNET VOLOS' unless otherwise noted, is based on observations taken during the 2011, 2012, and 2013 growing seasons(s) in Udine, Italy and Fossalon di Grado (GO), Italy. from plants dug from a nursery located in Rauscedo (PN), Italy during the beginning of December 2007 and planted approximately 16 to 20 weeks later in Udine, Italy and Fossalon di Grado (GO), Italy The phenotypical descriptions and color designations stated for the new variety may vary, depending upon variations in environmental factors, including weather (temperature, humidity and light intensity), day length, soil type, location and cultural conditions. 'CABERNET VOLOS' has not been observed under all possible environmental conditions.

Color references are made to The Royal Horticultural Society Colour Chart (R.H.S.), (Edition V, 2007), except where general colors of ordinary significance are used.

| Characteristic | 'CABERNET VOLOS' | 'CABERNET SAUVIGNON' (unpatented) |
|---|---|---|
| GENERAL | | |
| Resistance to pest/disease | Resistant to downy mildew, tolerant to powdery mildew | Susceptible to both downy and to powdery mildew |
| Resistance to natural elements | Resistant to winter cold down to −23° C. | Resistant to winter cold not evaluated |
| VINE | | |
| Vigor | medium | high |
| Trunk diameter | 6 cm (6 yrs-old plant) | 6 cm (6 yrs-old plant) |
| Bark | | |
| color | RHS 177B | Brownish |
| underbark color | RHS 179B | Light brown |
| texture | n.a. | n.a. |
| Canes | | |
| length | Internode length cm 13-14 | Internode length cm 10 |
| width | 9-10 mm | 8 mm |
| Shoots | | |
| shape | Semi-erect, cross section: elliptic, surface: with stripes, nodes and internodes without hairs | Horizontal, cross section: circular, surface: smooth, nodes and internodes without hairs |
| color | Internodes with red (RHS 185B) and green (RHS 144B) pigmentation on dorsal side,and green (RHS 144B) ventral side | internodes and nodes with green and red color on dorsal side and green pigmentation on ventral side |
| Tendrils | | |
| form | Bifid | bifid |
| color | RHS 145C and RHS 184D | Green |
| texture | normal | normal |
| number | 2 or <2 consecutive | 2 or less consecutive |

-continued

| Characteristic | 'CABERNET VOLOS' | 'CABERNET SAUVIGNON' (unpatented) |
|---|---|---|
| Buds | | |
| size | average | average |
| shape | round | round |
| color | RHS 139C and RHS181A | Light brown |
| number | 2/node | 2/node |
| time of budbreak | early | medium |
| LEAVES | | |
| Size | medium | medium |
| Number of leaflets | 5 | 5 |
| Glossiness | Medium-high | medium |
| Cross section shape | V-shaped | flat |
| Color (immature) | | |
| Upper surface | RHS 143B and RHS185B | copper-reddish |
| Under surface | RHS 143B and RHS185B | copper-reddish |
| Color (mature) | | |
| Upper surface | RHS 143B | medium green |
| Under surface | RHS 143C | medium green |
| Petiole | | |
| Length (cm) | 6.2 | 6.0 |
| Color (upper surface) | RHS 185D | reddish |
| Color (under surface) | RHS185D | reddish |
| Stipule orientation | n.a. | n.a. |
| FLOWERS | | |
| Flowering period (time of beginning of flowering) | End of May | 1st week June |
| Sex | hermaphrodite | hermaphrodite |
| Size | Average | average |
| Diameter (cm) | 0.3 (stamens) | 0.3 (stamens) |
| Stamen color | RHS 4D | |
| Pistil color | RHS 149A | |
| Fragrance | average | average |
| Flower number (at 3rd node from tip of lateral mean and range) | n.a. | n.a. |
| Petals | | |
| Length (cm) | n.a. | n.a. |
| Width (cm) | n.a. | n.a. |
| Overall shape | calyptra | calyptra |
| Calyptra Color | RHS 134A | green |
| Sepals | | |
| Length (cm) | n.a. | n.a. |
| Width (cm) | n.a. | n.a. |
| Overall shape | n.a. | n.a. |

-continued

| Characteristic | 'CABERNET VOLOS' | 'CABERNET SAUVIGNON' (unpatented) |
|---|---|---|
| Color (immature) | n.a. | n.a. |
| Upper surface | | |
| Under surface | | |
| Color (mature) | n.a. | n.a. |
| Upper surface | | |
| Under surface | | |
| Pedicel | | |
| Length (mm) | 45 (cluster) | 6 |
| Color | RHS 145C | green |
| FRUIT | | |
| Primocane time of fruiting (1st pick) | September 10th | September 27th |
| Clusters | | |
| cluster weight | g 130 | Small (g 139) |
| cluster shape | cylindrical | cylindrical |
| cluster length | mm 100 | medium (mm 195) |
| avg. berries per cluster | 120 | 99 |
| avg. clusters per shoot | 2 | 2 |
| Berries | | |
| Berry size | g 1.44 | Very low (g 1.4) |
| Berry length (cm) | 1.76 | 1.5 |
| Berry width (cm) | 1.56 | 1.5 |
| Overall shape of berry | globose | globose |
| Berry Texture | soft to slightly firm | soft |
| Berry Skin Color (immature) | RHS 137C | green |
| Berry Skin Color (mature, at 19° Bx) | RHS 103B | Blu black |
| Berry Flesh Color | RHS 148B | |
| Soluble solids (%) | 24.8 | 22.1 |
| Titratable acidity (as g/L tartaric acid) | 4.8 | 7.4 |
| Sugar/acid ratio | 5.2 | 3.0 |
| Firmness | soft | soft |
| Seeds | 2-3 | 2-3 |
| Seed Color | RHS 167B and RHS I63A | |
| Skin cracking? | no | no |
| Juice color | red | No or very weak |
| Berry taste | Slightly herbaceous | herbaceous |
| Eating quality | n.a. | n.a. |
| Berry uses | wine | wine |
| Shipping quality | n.a. | n.a. |

What is claimed is:

1. A new and distinct grapevine, referred to as 'CABERNET VOLOS', as herein described and illustrated by the characteristics set forth above.

* * * * *